United States Patent [19]

Sperry

[11] Patent Number: 5,441,174

[45] Date of Patent: Aug. 15, 1995

[54] STERILE WOUND CLEANSING DISPENSER WITH SPRAY SHIELD AND METHOD OF MAKING A DISPENSER

[76] Inventor: Charles R. Sperry, 113 Clinton St., Springfield, Vt. 05156

[21] Appl. No.: 47,816

[22] Filed: Apr. 15, 1993

Related U.S. Application Data

[63] Continuation-in-part of Ser. No. 873,952, Apr. 23, 1992, abandoned.

[51] Int. Cl.$^6$ .............................................. B65D 35/56
[52] U.S. Cl. .................................. 222/105; 222/212; 222/183; 222/386.5
[58] Field of Search ............... 222/92, 105, 107, 183, 222/206, 212, 215, 386.5; 128/66; 604/132, 289, 290

[56] References Cited

U.S. PATENT DOCUMENTS

| | | |
|---|---|---|
| 1,178,898 | 4/1916 | Young . |
| 1,602,215 | 10/1926 | Smith . |
| 1,889,425 | 11/1932 | Sorensen . |
| 2,626,606 | 1/1953 | Campbell .......................... 222/212 X |
| 2,771,072 | 11/1956 | Montauge ............................ 128/241 |
| 3,361,303 | 1/1968 | Jacuzzi ............................ 222/212 X |
| 3,848,808 | 11/1974 | Fetty et al. ......................... 239/327 |
| 3,876,115 | 4/1975 | Venus, Jr. et al. .................. 222/183 |
| 3,912,168 | 10/1975 | Mullins et al. ...................... 239/102 |
| 3,993,054 | 11/1976 | Newman ............................... 128/66 |
| 4,222,499 | 9/1980 | Lee et al. ............................ 222/183 |
| 4,235,265 | 11/1980 | Feliks .................................. 141/85 |
| 4,301,798 | 11/1981 | Anderson ............................ 128/239 |
| 4,375,145 | 3/1983 | Mosse et al. .......................... 53/425 |
| 4,387,833 | 6/1983 | Venus, Jr. ............................ 222/95 |
| 4,423,829 | 1/1984 | Katz ..................................... 222/95 |
| 4,458,830 | 7/1984 | Werding ............................. 222/131 |
| 4,465,479 | 8/1984 | Meisch ................................. 604/251 |
| 4,524,563 | 6/1985 | Sassi .................................... 53/462 |
| 4,555,645 | 11/1985 | Atkinson ............................. 310/27 |
| 4,561,431 | 12/1985 | Atkinson ............................. 128/66 |
| 4,635,621 | 1/1987 | Atkinson ............................. 128/66 |
| 4,676,279 | 6/1987 | von Lersner ........................ 141/1 |
| 4,692,140 | 9/1987 | Olson .................................. 604/40 |
| 4,784,637 | 11/1988 | Ryder et al. ......................... 604/32 |
| 4,805,378 | 2/1989 | Anderson ............................. 53/426 |
| 4,821,924 | 4/1989 | Kozam ................................ 222/211 |
| 4,942,716 | 7/1990 | Anderson ............................. 53/426 |
| 4,953,753 | 9/1990 | Gortz .................................. 222/105 |
| 4,964,540 | 10/1990 | Katz ..................................... 222/95 |
| 4,994,065 | 2/1991 | Gibbs et al. ......................... 606/92 |
| 4,999,978 | 3/1991 | Kohlbach et al. .................... 53/512 |
| 5,133,701 | 7/1992 | Han .................................... 222/389 |
| 5,143,263 | 9/1992 | Newell ................................ 222/538 |
| 5,269,428 | 12/1993 | Gilbert ............................... 222/105 X |

FOREIGN PATENT DOCUMENTS

| | | | |
|---|---|---|---|
| 3935818A1 | 5/1991 | Germany ............................ 604/290 |
| 63-294378 | 12/1988 | Japan ................................. 222/386.5 |

OTHER PUBLICATIONS

New Day-Wash Skin Wound Cleanser Brochure, Dey Laboratories, Inc., 1991.
Zerowet Splashield Brochure, Zerowet, Inc., 1991.
Irrijet Brochure, Ackrad Laboratories, Inc.
Ultra-Klenz Advertisement by Carrington Laboratories, Inc. May/June 1991, Ostomy/Wound Management.
The Akro System Brochure, Akron Polymer Container Corporation.

(List continued on next page.)

*Primary Examiner*—Andres Kashnikow
*Assistant Examiner*—Joseph A. Kaufman
*Attorney, Agent, or Firm*—Davis Hoxie Faithfull & Hapgood

[57] ABSTRACT

A wound cleansing solution dispenser that indicates the volume of liquid remaining and reduces medical waste. A shield is mounted onto the dispenser to prevent any contaminated fluids from splashing onto the care giver. The dispenser can be brought in a sterile condition to the patient free from any separate power supplies or fluid source lines. The stream pressure of the dispenser may be adjustable but it may be set for a substantially constant pressure over the volume of fluid. The dispenser may be used in any orientation and still deliver wound cleansing solution at the selected pressure.

20 Claims, 7 Drawing Sheets

OTHER PUBLICATIONS

"Exxel: The Ultimate Delivery System", Exxel Technical Documentation Series, Product Information Bulletins, Exxel, Inc., 1990.

Woolston, J., "Irradiation Sterilization of Medical Devices", Medical Device Technology, Jul./Aug. 1990.

"Tricks of the Trade: Splash Protection", Emergency Medicine, Dec. 15, 1990, p. 50.

"Technology Watch: Wound Cleanser", Decubitus, May 1991, vol. 4 No. 2, p. 80.

Christiansen, S., "The Future of Aerosols?", Soap/Cosmetics/Chemical Specialties for Jul. 1990, pp. 26–27.

Isomedix Brochure, Isomedix Inc.

Morrissey, R. F., et al., "Sterility and Safety Assurance of Medical Devices", Medical Device & Diagnostic Industry, Apr. 1992, pp. 78–81.

Dire, D., "A Comparison of Wound Irrigation Solutions Used in the Emergency Department", Annals of Emergency Medicine, Jun. 1990, pp. 704–708.

Rodeheaver, G., et al., "Wound Cleansing by High Pressure Irrigation", Surgery, Gynecology & Obstetrics, Sep. 1975, vol. 141, pp. 357–362.

Wheeler C., et al., "Side-Effects of High Pressure Irrigation", Surgery, Gynecology & Obstetrics, Nov. 1976, vol. 143, pp. 775–778.

Gross, A., et al.,"Effectiveness of Pulsating Water Jet Lavage in Treatment of Contaminated Crushed Wounds" Am. J. Surg. 1972; 124:373–377.

Lammers, R., "Principles of Wound Management", in Roberts & Hedges, eds., Clinical Procedures in Emergency Medicine, pp. 478–530 (W. B. Saunders, Philadelphia 1985).

Edlich, R., et al., "Principles of Emergency Wound Management" Annals of Emergency Medicine, 17:12 Dec. 1988, pp. 1284–1302.

Peacock, E., "Repair of Skin Wounds", Wound Repair, 1984, pp. 143–147.

Berk, W. A., "Evaluation of the 'Golden Period' for Wound Repair: 204 Cases From a Third World Emergency Department", Annals of Emergency Medecine, May 1988, pp. 496–500.

Tobin, G. R., "Closure of Contaminated Wounds", Surgical Clinics of North America, vol. 64, No. 4, Aug. 1984, pp. 639–652.

Skiens, W. E. "Sterilizing Radiation Effects on Selected Polymers", Report No. CONF 7903108-1, presented at the Symposium on radiation sterilization of plastic medical products on Mar. 28, 1979.

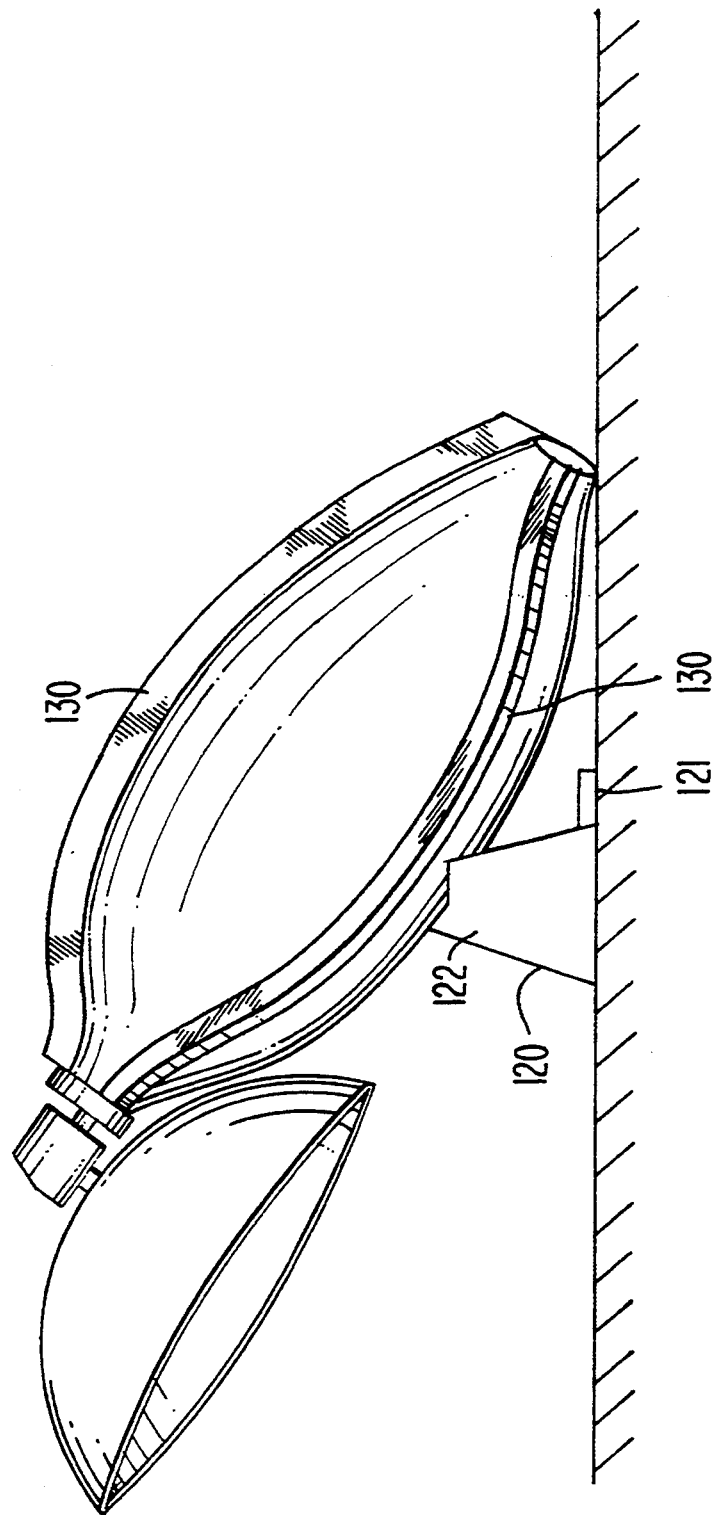

STERILE WOUND CLEANSING DISPENSER WITH SPRAY SHIELD AND METHOD OF MAKING A DISPENSER

This application is a CIP of U.S. Ser. No. 07/873,952, filed Apr. 23, 1992 now abandoned.

FIELD OF THE INVENTION

This invention relates generally to wound cleansing. More particularly, the present invention relates to portable dispensers of wound cleansing fluid.

BACKGROUND OF THE INVENTION

Patients often have open wounds that must be cleaned of dirt and other foreign particles before closing. Sometimes wounds must be cleaned several times. In known wound cleansing procedures, a stream of sterile cleansing fluid is directed through a nozzle at the wound. Wound cleansing solutions, well known in the art, generally are saline solutions, typically 0.9% sodium chloride. When a cleansing solution is not to be used within a matter of hours, a preservative such as benzalkonium chloride may be included. Additives such as buffers may be included as well. If the stream impacts the wound within a limited pressure range of about 8-15 psig, the pressure stream dislodges foreign particles in the wound and washes them away, but does not tear away living tissue. It is also known to use fluid streams at substantially lower or higher pressures.

Several systems and devices for delivering a stream of fluid to a wound are known. Some systems are fixed installations. See, e.g., U.S. Pat. Nos. 3,912,168, 4,692,140, and 4,635,621. Others utilize "portable" dispensers; that is, dispensers that can be carried by hand to the patient without being attached either to a separate power supply or to a fluid supply. Typically a wound requires upwards of 200 ml of fluid to be cleaned properly.

One known apparatus of the fixed installation type consists of a syringe with a flexible plastic tip for aiming the fluid stream. One end (sharpened) of a tube attached to the syringe is spiked into an IV bag, a source of cleansing fluid. As the syringe piston is retracted by the care giver, the syringe fills with cleansing liquid. When the care giver presses on the piston, the liquid is forced out the flexible plastic tip. A rigid splash shield may be positioned on the syringe near the tip to prevent splashback onto the care giver. This device has several disadvantages. It requires the care giver to remain near the fluid supply, the IV bag, because the syringe, which holds only 10 or 30 cc of fluid, remains attached to the IV bag during use. The care giver must pump repeatedly with his thumb to clean a single wound. The pressure of the liquid stream is not fixed. Rather, it depends on the thumb pressure applied to the piston by the care giver. If the care giver does not depress his thumb with enough force, the pressure of the stream will be insufficient to dislodge particles.

Another fixed installation commercially marketed is the Pulsavac ®, manufactured by Bristol-Myers Squibb Co., purportedly under U.S. Pat. Nos. 4,555,645; 4,561,431; 4,635,621; and 4,692,140. This apparatus includes an electric pump that delivers wound cleansing liquid through a long, flexible tube to a hand-held dispensing gun. Another tube (sharpened) attached to the pump is spiked into a bag of wound cleansing solution. The pump is capable of delivering liquid in a pulsing manner (adjustable to a maximum pressure of 70 psig) through the delivery tube to the dispensing gun. The care giver holds the gun and "shoots" cleansing fluid at the wound. The dispensing gun comes with several attachments, including a spray shield that attaches to the tip of the gun. The shield consists of an inner flexible cone and, optionally, an outer rigid cone. The cones trap fluids exiting the wound between them so that they can be removed by a vacuum tube mounted in the gun.

This apparatus has several disadvantages. The dispensing gun must be used near the pump because of the delivery and vacuum tubes. Further, the tubes, if of appreciable length, drag across the floor, generally a hospital floor. Also, the apparatus creates considerable medical waste. After each use, the entire gun/spray shield combination is discarded. The pump and tubes must be disposed of after 24 hours.

Aerosol dispensers are known for use as portable dispensers of wound cleansing solution. Two commercially available dispensers are the Dey-Wash ® aerosol sprayer marketed by Dey-Wash Corporation and the Baxter Skin Wound Cleanser marketed by Baxter Healthcare Corporation. Both utilize rigid aerosol cans. The Dey-Wash aerosol can contains a bag filled with cleansing liquid. The aerosol dispensers are operated in the conventional manner. A straw may be fitted onto the outlet of the nozzle to help direct the fluid.

Aerosol dispensers overcome one major disadvantage of fixed installations, namely, lack of portability. However, they also have distinct disadvantages. They create considerable medical waste. For the available aerosol systems described above, a dispenser is used only on a single patient, after which the can, other parts and materials become waste. An empty aerosol dispenser is just as large as a full one, so the volume of waste is large. Aerosol dispensers may have other disposal problems, as is well known, including the problem that metal aerosol cans can not be incinerated. The noted commercially available aerosol devices do not come with a splash shield, so contaminated or infected fluid may splash onto the care giver and the dispenser. Another drawback to this device is that the care giver cannot determine visually how much wound cleansing solution remains in the container. With the commercially available aerosol dispensers, the care giver cannot adjust the force with which the fluid is dispensed. Importantly, the stream pressure is not as nearly constant as desirable as the dispenser is emptied.

It is an object of this invention to provide a wound cleansing apparatus having the advantage of the aerosol dispensers, namely, portability, without the disadvantages of those dispensers.

It is another object of this invention to provide a portable wound cleansing apparatus capable of delivering a liquid stream of wound cleaning fluid at a substantially constant pressure of 8 psig and, optionally, at that pressure and at additional pressures selected by the care giver.

It is yet another object of this invention to provide a wound cleansing device that also protects the care giver from fluid splashing off the wound.

It is yet another object of this invention to provide a portable wound cleansing device which provides visual indication of how much wound cleansing liquid remains in the device.

It is yet another object of this invention to provide a portable wound cleansing device that minimizes medical waste and, further, produces a type of waste with minimal disposal problems.

It is yet another object of this invention to provide a portable wound cleansing device that can be operated with conventional nozzles that are readily commercially available to provide wound cleaning solution at a controlled pressure.

It is yet another object of this invention to provide an improved portable wound cleansing device that is sterile, so that it may be used in sterile fields, such as hospital emergency rooms and operating rooms.

These and other objects of the invention will become apparent to those working in the art by reference to the following description, including the accompanying drawings.

SUMMARY OF THE INVENTION

This invention comprises an improved wound cleansing apparatus that is portable, i.e., it can be taken to a patient free of any power line or fluid source line. A liquid wound cleansing solution reservoir in the form of an inflatable bag is disposed within an elastomeric tube. As the bag is filled with wound cleansing solution, the bag inflates, thereby expanding the elastomeric tube. The tube then exerts pressure on the fluid in the bag as it seeks to regain its original shape. An actuatable valve is mounted in an opening in the bag. A nozzle-actuator is mounted on the outlet of the valve. When the valve is actuated by depressing the nozzle, cleansing fluid is forced by the pressure in the bag through the valve and nozzle. The nozzle directs the fluid stream. The liquid stream pressure is substantially constant as the bag is emptied. As cleansing solution is dispensed, the tube returns to its original shape, i.e., it shrinks. The size of the tube provides to the care giver an easily observable visual indication of the amount of fluid remaining. Splashing fluids are contained and prevented from reaching the care giver by a large transparent flexible splash shield mounted on the nozzle.

The device contains a minimum amount of metal and hard plastic. It comprises no rigid container. The volume of waste is minimized due to the fact that the device shrinks substantially as it is emptied. The bag and, more importantly, the elastomeric tube have a high heat content and contribute to burning.

The filled device may be sealed within a sterilizable pouch, after which the device and pouch may be sterilized together, such as by irradiation with gamma radiation. The pouch material is selected so that after sterilization the pouch maintains the device, and thus the wound cleansing solution in the device, in a sterile condition.

The device may include a nozzle that delivers a substantially constant liquid stream pressure of about 8 psig at the extent of the splash shield. As would be well understood in the art, the stream pressure is dependent upon the pressure in the container as well as the design of the nozzle. Alternately, the device may include a nozzle capable of delivering additional stream pressures selectable by the care giver. For instance, the nozzle may be designed to provide an infinitely variable pressure up to a preselected maximum pressure.

BRIEF DESCRIPTION OF THE DRAWINGS

FIG. 7 is a side view of a dispenser of this invention having spokes and mounted on a stand.

DETAILED DESCRIPTION OF PREFERRED EMBODIMENTS

Figure 1:
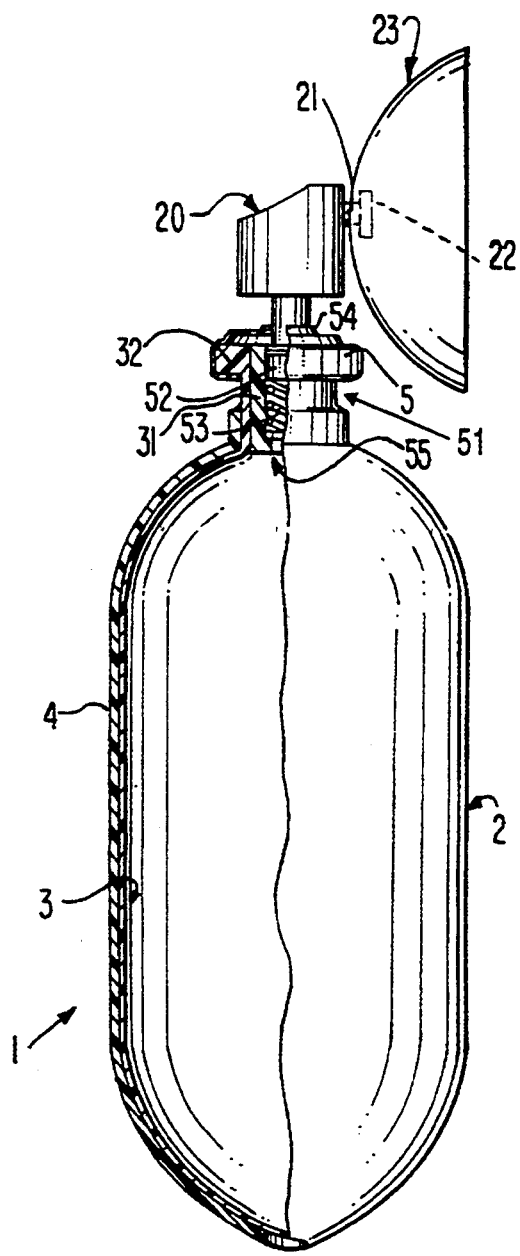
FIG. 1 is a side view of the dispenser of this invention showing a partial cutaway view of the container.

FIG. 1 shows a portable wound cleansing dispenser 1 for dispensing sterile wound cleansing fluids according to a preferred embodiment of this invention. Dispenser 1 comprises a sterile container 2 that includes an expandable, leak-proof bag 3, a cylindrically shaped thick-walled elastomeric tube or sleeve 4, and a valve assembly 5. Valve assembly 5 is sealingly mounted into a mouth in bag 3, forming a normally closed pressurizable chamber for receiving, holding and dispensing cleansing fluid.

Removably mounted on valve assembly 5 is a plastic, disposable actuating spray nozzle 20 including a shield mounting post 21 and shield retaining button 22. The nozzle 20 is finger-operable. Spray shield 23 contains a deformable slot (not shown) such that shield 23 can be snapped over button 22 onto post 21. Nozzle 20 and spray shield 23 are sterilizable and disposable. Dispenser 1 is shown in FIG. 1 in its assembled configuration with bag 3 containing fluid such that sleeve 4 is expanded.

Container 2, including bag 3, sleeve 4 and valve assembly 5, is a substantially constant delivery pressure, elastomeric container of the type marketed by Akron Polymer Container Corporation of Akron, Ohio under the name of Akro ® System. Another acceptable container is described in U.S. Pat. Nos. 4,423,829 and 4,964,540, both incorporated herein by reference, and marketed by Exxel/Atmos Containers, Inc. of Somerset, N.J. under the name Exxel TM Container. Containers for the Akro ® System and the Exxel TM Containers have been used commercially as inner containers, mounted in cans, forming a part of dispensers for products other than a wound cleanser.

Container 2 has a delivery pressure that is essentially flat, i.e., within a range of only about 0.6 psig, over the majority of its volume. Further, it has a delivery pressure within one psig of selected pressure over very close to two-thirds of its volume. Further, the delivery pressure falls off precipitously rather than gradually as the container is nearly emptied. In other words, after reaching the flat portion of the curve, the delivery pressure stays within 2 psig of the selected pressure until the container is about 95% emptied (12 ml remaining from an initial charge of about 240 ml), thereby making nearly all of the contained fluid useful for wound cleansing. As used herein, "substantially constant delivery pressure" means the type of delivery just described.

Bag 3 is a flexible, non-elastomeric, generally cylindrical fluid container comprising a non-reactive, non-contaminating material that is compatible with the wound cleansing liquid during storage and use. The Exxel TM container is believed to contain bag 3 made of polyethylene terephthalate. Other suitable materials identified in U.S. Pat. No. 4,964,540 include nylon and polypropylene. Sleeve 4 is an expandable elastomeric cylinder coaxially enclosing bag 3. The Exxel ™ container is believed to contain a sleeve 4 made of natural rubber or natural latex. Spray shield 23 is made of a styrene ethylene-butylene styrene block copolymer sold by Concept Polymer Technologies, Inc. under the trademark C-FLEX ®. Spray shield 23 could also be made of PVC.

Bag 3 preferably is pleated and folds onto itself as fluid is expelled without creating creases that would trap fluid. According to U.S. Pat. No. 4,423,829, such a bag 3 is preferably formed by blow molding a vessel which has a star-shaped cross section. Bag 3 preferably has a latex coating that prevents the bag from slipping out of sleeve 4. According to U.S. Pat. No. 4,423,829, the coating is formed by dipping bag 3 in latex. According to U.S. Pat. No. 4,423,829, a sheath may be disposed about bag 3 where no latex coating is used. The sheath, whose design is described in said patent, expands radially but not longitudinally.

Figure 2:
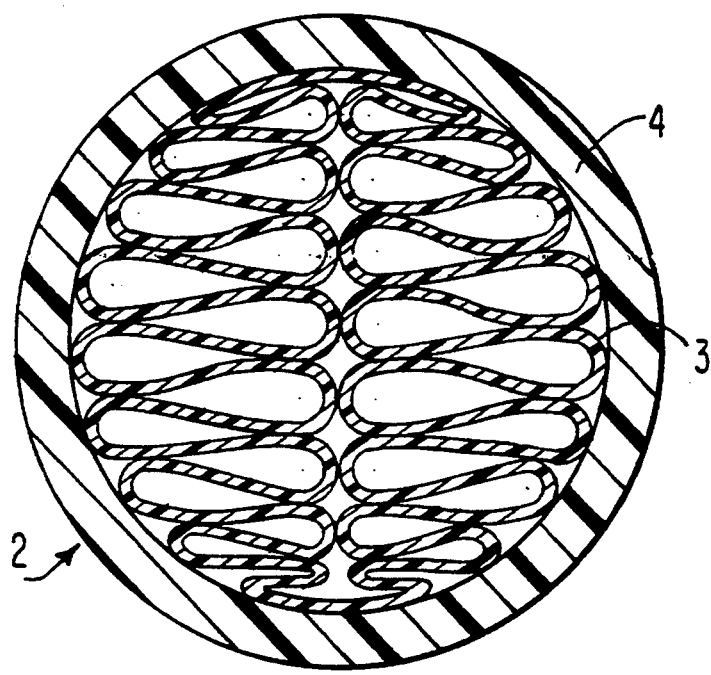
FIG. 2 is a cross sectional view of the dispenser of this invention without wound cleansing solution.

FIG. 2 shows in cross section a container 2, which in this embodiment is the Akro ® System container. Bag 3 is formed by blow molding a vessel which folds roughly symmetrically about a diameter of sleeve 4 when empty of wound cleansing solution. Bag 3 may be made of polyethylene and need not be coated with latex. Further, a sheath need not be disposed about the bag. Rather, bag 3, is directly enclosed by sleeve 4, made of polyisolene. Both the Exxel ™ and the Akro ® System containers have been found acceptable for use with the present invention.

Again referring to FIG. 1, the open mouth of bag 3 comprises neck 31 and molded terminal circular flange 32. Neck 31 is sealingly engaged to valve assembly 5 by crimping the valve assembly over flange 32 to prevent the valve assembly from being disengaged from bag 3 due to pressure in the bag.

Valve assembly 5 is of known design. As described in U.S. Pat. Nos. 4,423,829 and 4,964,540, valve assembly 5 contains a valve 51 having a cylindrical passage 55 normally closed by circular valve disk 52 biased by spring 53. Raised mounting lip 54 concentrically spaced from passage 55 receives nozzle 20. It will be noted that the ends of sleeve 4 are not closed. This allows bag 3 to extend beyond the sleeve 4 when uninflated and causes sleeve 4 to expand without buckling when inflated.

Figure 3:
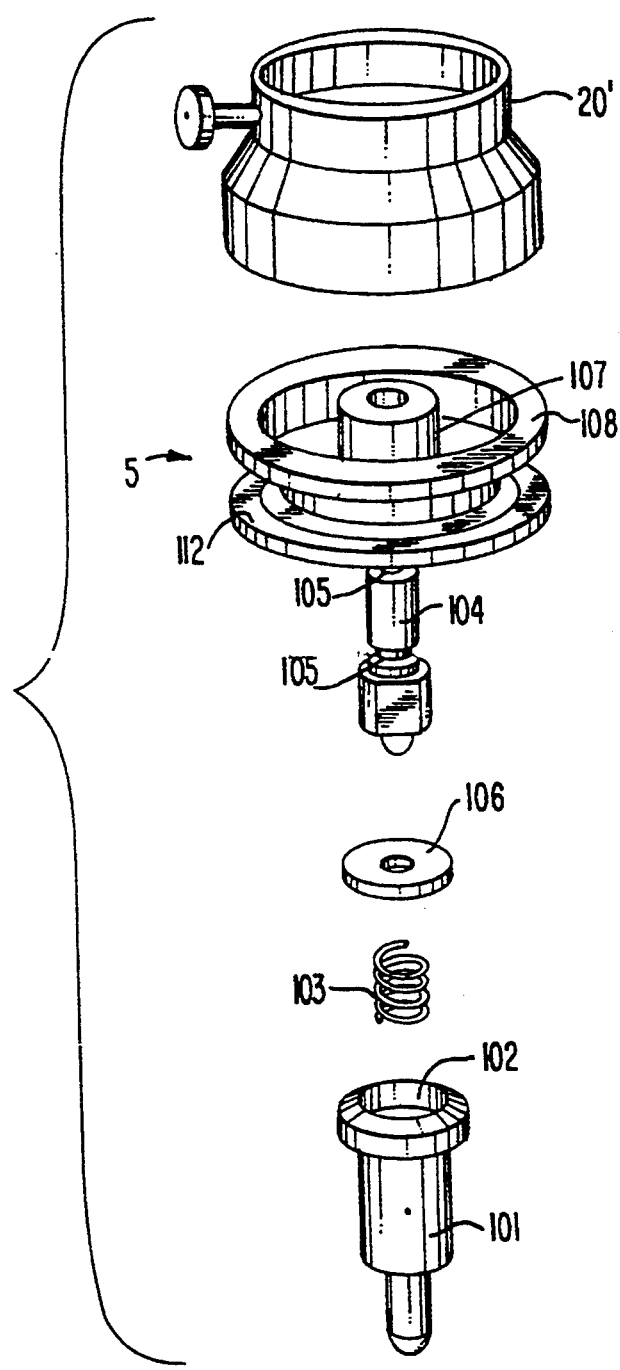
FIG. 3 is an exploded view of a valve assembly of the present invention.

FIG. 3 shows an exploded view of an alternate valve assembly 5' marketed commercially by the Precision Valve Corporation and suitable for use with the Akro ® System container including nozzle 20' (Precision Valve Corporation part #22-1226), body 101 (Precision Valve Corporation part #07-0166), spring 103 (Precision Valve Corporation part #06-6010), stem 104 (Precision Valve Corporation part #04-1238) and gasket 106 (Precision Valve Corporation part #05-0410). A cylindrical body 101 contains body passage 102. Spring 103 is seated in body passage 102. Stem 104 is positioned in body passage 102 in sliding engagement with body 101 such that spring 103 resists movement of the stem toward the body. A stem passage 105 is located in stem 104 leading from the side of the stem disposed within body passage 102 to the top of the stem outside the body passage.

Stem gasket 106 is disposed in body passage 102 about stem 104 such that stem passage 105 at the side of the stem is blocked by the gasket when the stem is not depressed. Stem 104 is positioned in a mounting cup 107 such that the top of the stem protrudes above the top of the cup when assembled. Rim 108 is disposed about mounting cup 107. Mounting ring 112 is positioned beneath rim 108.

Valve assembly 5' is mounted to neck 31 of bag 3. Neck 31 is disposed between rim 108 and mounting ring 112. Rim 108 is crimped onto neck 31 and ring 112, forming a fluid-tight seal such that fluid may not leak between the neck and mounting cup 107.

Nozzle 20' mounts onto the top of stem 104 such that depressing the nozzle causes the stem to overcome the bias of spring 103 and slide within body passage 102. Stem gasket 106 flexes, uncovering stem passage 105 and permitting fluid flow through body passage 102. Consequently, stem gasket 106 and stem 104 cooperate to form a valve that selectively permits flow through valve assembly 5'.

An advantage of the valve assembly 101 is that it is composed of commercially available parts sized to accept standard nozzles 20' from various nozzle manufacturers. Such a standard nozzle 20' is described more fully below in conjunction with FIG. 4. Nozzles 20' are commercially available in many designs and sizes which result in different fluid stream pressures.

Container 2 is filled by conventional means. To fill container 2, fluid is pumped into bag 3 through valve assembly 5. Pressure from fluid inside bag 3 expands the bag and elastomeric sleeve 4 to their expanded form shown in FIG. 1. Because it is elastic, sleeve 4 creates pressure on bag 3. Valve disk 52 is normally biased by valve spring 53, preferably stainless steel, to seal passage 55, thereby closing container 2. Filled container 2 can be fitted with a nozzle 20 to create a dispenser 1. Alternatively, of course, container 2 can be filled through nozzle 20.

In the alternative embodiment of valve assembly 5' shown in FIG. 3, spring 103 biases stem 104 away from body 101. Stem gasket 106 is thus in the unflexed position, blocking the stem passage 105. To fill container 2, stem 104 is depressed, pulling stem gasket 106 away from stem passage 105. Fluid is then pumped into stem 104, through body passage 102 and into bag 3. When filling is complete, stem 104 is released such that spring 103 can bias the stem away from body 101. Consequently, gasket 106 returns to its unflexed position blocking stem passage 105 and maintaining the fluid in bag 3.

Shield 23 should be relatively transparent so that the care giver can observe the course of wound cleaning through the shield while being protected from splattering from the wound. The shield could be flat, e.g., a disk, but a shield in the shape of a segment of a sphere is preferred for containment of splattering. Shield 23 is approximately four inches wide and about 2.5 inches deep. Shield 23 is flexible for better packaging and so that it may conform to the body contour near the wound. A rigid shield that does not deform when placed around a wound is much less preferred. The dispenser 1 is, of course, operative without a shield 23, but that is definitely not preferred. Optionally, shield 23 may be coated on the side facing the wound with a wetting agent to improve visibility.

To use a filled dispenser 1, a care giver places the spray shield 23 over the wound. Holding container 2 in one hand, the care giver depresses nozzle 20 with his or her thumb or index finger. Nozzle tip 47 (see FIG. 2) depresses valve disk 52, overcoming the bias of valve spring 53 and moving disk 52 away from sealing engagement. Cleansing fluid flows through the cylindrical passage 55 into nozzle 20. Alternatively, in the valve assembly 5' of FIG. 3, stem 104 pulls away from gasket 106, allowing fluid flow through stem passage 105 and into nozzle 20'. As described more fully bellow, a narrow stream of cleansing fluid is directionally expelled from nozzle 20 and directed at the wound.

Cleansing solution ejecting from nozzle 20 contacts the wound at a particular design stream pressure or pressures, most preferably being or including a substantially constant stream pressure of about 8 psig at the wound, to wash away particles embedded in the wound without significant tissue damage. By "about 8 psig" is meant greater than 4 psig and no more than 15 psig. One skilled in the art would well understand that the resultant stream pressure is determined by the pressure of the solution in the container as well as the design of the nozzle. Consequently, a nozzle is selected or designed in view of sleeve 4 to deliver desired flow and force. Splatter from the wound is blocked by the shield 23. Consequently, the care giver is not exposed to contaminated or infected fluids. Because splash shield 23 is transparent, the care giver can see where to move the stream to clean the wound completely.

After use on one patient, the nozzle 20 and shield 23 are disposed of. If container 2 has been only partially emptied on a first patient, it can be reused by adding a sterile replacement nozzle 20 and replacement shield 23 to create a new dispenser 1 for use on a second patient. In this way, container 2 need not be disposed of after treating one patient if fluid remains. It is preferred that container 2 holds 200–250 ml, in which case it will typically have only enough fluid for one patient and also will be disposed of. Depending on the size of the container 2 in comparison to the service use of the device, one may elect to provide replacement nozzles/shields or not to do so. It should be noted that a small amount of residual fluid will not expel at sufficiently high pressure once the container becomes almost empty. As a result, a small amount fluid will remain unused.

The wound cleansing fluid dispenser of the present invention offers numerous advantages over existing dispensers and systems. As compared to fixed installations, the dispenser according to this invention has advantages of portability, cost and waste generation. As compared to portable aerosol dispensers, the dispenser of this invention is capable of delivering a stream of fluid at a more substantially constant pressure, and protecting the care giver from splashing fluids while allowing the care giver to view the cleansing process. This invention also permits the care giver to know how much wound cleansing solution remains in the container merely by looking at the container, since the size of the container reduces as the fluid is expelled. Further, the dispenser expels fluid when held in any position. An aerosol with a dip tube rather than a more expensive inner bag must be held relatively upright.

The wound cleaning fluid dispenser of the present invention offers significant storage and disposal advantages over aerosol wound cleansing dispensers. The sleeve 4 serves as an outer wall of the dispenser, and, thus, there is no additional can to be disposed of. This also reduces storage space required and shipping costs because the dispenser is smaller and lighter than if it were packed in a can. Preferably, the dispenser is constructed of materials that can be easily disposed of. Bag 3 and sleeve 4 are preferably burnable without serious toxicity problems and, furthermore, are of high heat content, whereas aerosol cans are difficult and expensive to have carted away and cannot be incinerated. Very importantly, since the dispenser of this invention shrinks with use, there is significantly less bulk to have carted away as compared with aerosol dispensers. This reduces the relative overall cost of using the dispenser of this invention.

A staff may be mounted within the bag 3 such that there is practically no space between the bag and the staff when the bag is not expanded so as to minimize unused fluid. Numerous other variations are possible, as one skilled in the art will recognize. It is important that the portion of container 2 in contact with cleansing fluid is sterile, not reactive with cleansing fluid, and not leachable of harmful chemicals by the fluid.

Figure 4:
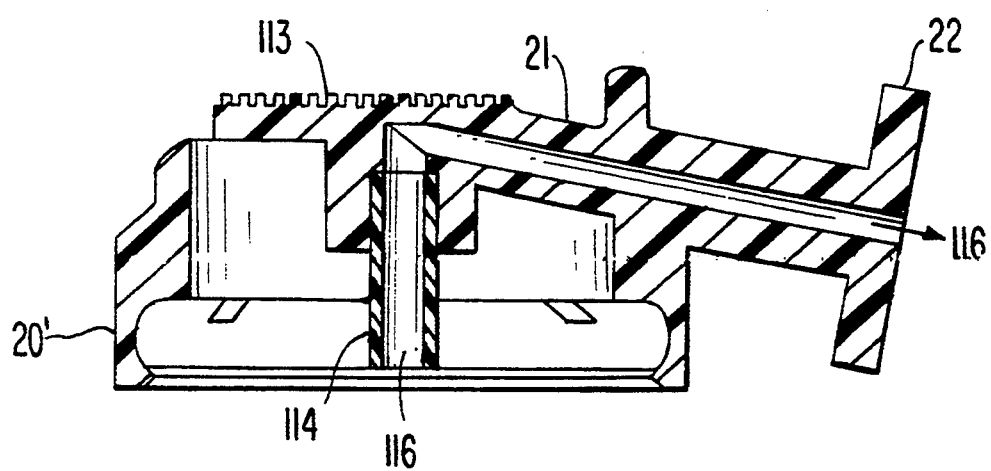
FIG. 4 is a cutaway view of a one stage nozzle of the present invention.
Figure 5:
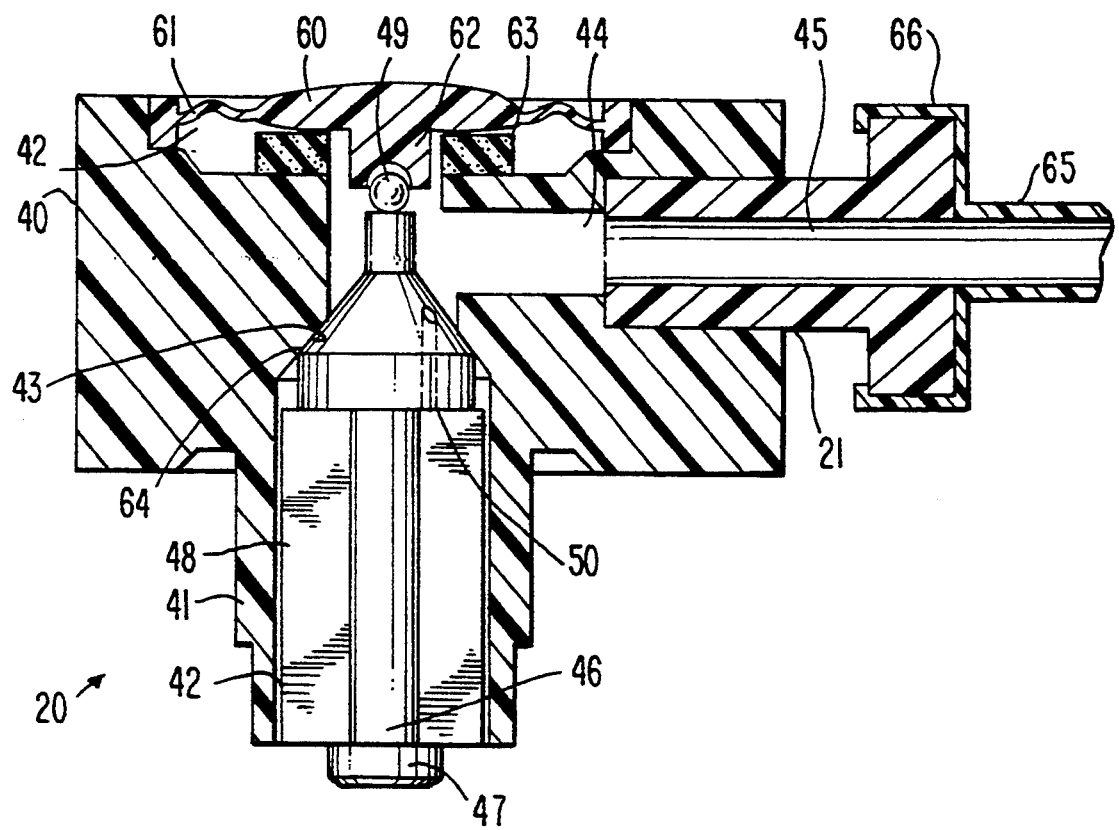
FIG. 5 is a cutaway view of a two stage nozzle of this invention.

A nozzle of conventional design, such as the one shown in FIG. 4, can be selected to produce a constant stream pressure, preferably about 8 psig, or to produce a pressure of varying strength as selected by the care giver. In an alternate embodiment, shown in FIG. 5, the nozzle 20 is designed so that it can produce a stream of fluid at a low pressure (2–4 psig) at a first setting and produce a stream at a substantially constant high pressure (8 psig) at a second setting. Nozzle 20 comprises head 40 mounted on cylindrical throat 41. Throat 41 is designed so that it fits loosely in valve assembly 5 (FIG. 1) such that nozzle 20 may translate up and down along the axis of the valve 51.

A rod chamber 42 is disposed along the axis of throat 41 and extends up through the top of head 40. In head 40, rod chamber 42 tapers, forming tapered section 43. Above tapered section 43, an exit bore 44 extends perpendicularly out from rod chamber 42.

Mounting post 21 and shield retaining button 22 are formed in a single piece. Mounting post 21 fits snugly into the exit bore 44 such that it remains there during operation of the dispenser, held in place by friction. A post bore 45 is disposed along the axis of mounting post 21 and connects exit bore 44 to the exterior of head 40.

A valve rod 46 is seated in rod chamber 42. Lower tip 47 of rod 46 extends below throat 41. In throat 41, wings 48 are mounted on and extend radially out from rod 46 to the edge of rod chamber 42. As explained below, rod 46 moves axially in chamber 42. Wings 48 prevent rod 46 from moving off center.

In tapered section 43, rod 46 is tapered to create a tapered surface 64 that sealingly engages tapered section 43 of rod chamber 42. A bead 49 is mounted at the top of rod 46. A shunt hole 50 is located in rod 46 and creates a passage through the rod at tapered section 43.

A finger pad 60 is mounted to head 40 by a peripheral web 61. Peripheral web 61 extends out from finger pad 60 and is heat-sealed to head 40, thereby sealing rod chamber 42 such that fluid cannot escape from the top of head 40. Web 61 is flexible so that finger pad 60 can be depressed into rod chamber 42.

A bead cup 62 is mounted on the underside of finger pad 60 directly above rod 46. Bead cup 62 engages bead 49 in snug fit when finger pad 60 is depressed. A sponge spring 63 is mounted between head 40 and finger pad 60 such that, to depress the finger pad into the head, the sponge spring must be compressed.

To operate nozzle 20 the care giver places spray shield 23 over the wound and depresses finger pad 60. Sponge spring 63 is sufficiently stiffer than valve spring 53 (FIG. 1) that, when finger pad 60 is depressed, nozzle 20 and rod 46 move down together, maintaining the seal in tapered section 43. The lower tip 47 of nozzle 20 contacts and displaces the valve disk 52. Displacing valve disk 52 permits fluid to flow from bag 3, through cylindrical passage 55, to rod chamber 42. A fluid flow path is defined by rod chamber 42, exit bore 44, and post bore 45. To operate nozzle 20 in the low pressure setting, finger pad 60 is depressed until head 40 contacts cap 5. Since tapered section 43 is sealed by tapered surface 64 of rod 46, fluid passes beyond tapered section 43 only by passing through shunt hole 50. The fluid exiting shunt hole 50 passes to exit bore 44, then to post bore 45, and then out of shield retaining button 22. Nozzle 20 is designed such that the exiting fluid has a stream pressure of 2–4 psig at the wound. Persons skilled in the art of nozzle construction will be able to design a nozzle to provide the desired stream of pressure for a particular container 2.

To operate nozzle 20 in the high pressure setting, finger pad 60 is depressed further. As noted above, head 40 has already contacted cap 5 and cannot move further down. Consequently, finger pad 60 is pushed into head 40 such that sponge spring 63 is compressed. Bead cup 62 contacts bead 49 and forces valve rod 46 to move down with respect to chamber 42. Tapered surface 64 of rod 46 disengages tapered section 43 of chamber 42, breaking the seal. Fluid now flows freely in the chamber 42, around rod 43 and into exit bore 44. A fluid pressure of 8 psig at the wound results.

Nozzle 20' of FIG. 4 is used with valve assembly 5' of FIG. 3. Flow conduit 114 of nozzle 20' is mounted on the top of stem 104. Finger pad 113 is disposed on the top of nozzle 20' adapted so that depressing the finger pad causes flow conduit 114 to move toward stem 104. Mounting post 21 and shield retaining button 22 are mounted on nozzle 20'. Fluid flow passage 116 runs through the flow conduit 114 and through mounting post 21, exiting through shield retaining button 22.

To operate nozzle 20' finger pad 113 is depressed, thus causing flow conduit 114 to move toward stem 104. Flow conduit 114 displaces stem 104 such that the stem slides within passage 102 overcoming the bias of spring 103. Consequently, gasket 106 disengages stem 104, opening the stem passage 105, permitting fluid flow through valve assembly 5' as described above. The fluid flows through body passage 102, to stem passage 105 and then to nozzle flow passage 116. Nozzle 20' directs the fluid stream out of mounting post 22 toward a wound.

Nozzle 20, as indicated previously, may have only a single setting, in which case it should be designed or selected to give a fluid stream of pressure of about 8 psig at the wound. Alternatively, nozzle 20 may have more than two settings and may even be infinitely variable as nozzle 20'. Infinitely variable nozzles are known. The keys with respect to nozzle 20 are two: it must be single-hand operable and must include a setting that provides a stream of pressure of about 8 psig measured at the wound.

A preferred embodiment of dispenser 1 includes a removably attachable extender tube to direct cleansing fluid into crevices, abscesses and body cavities, and particularly under skin flaps. Extender tube 65, also shown in FIG. 6, may be attached onto shield retaining button 22. Tube 65 is held in place by a tube flange 66 that slips over and engages button 22. Preferably, tube 65 is about four inches long. Tube 65 should not be so long or so narrow as to substantially reduce the stream pressure of the exiting fluid.

Figure 6:
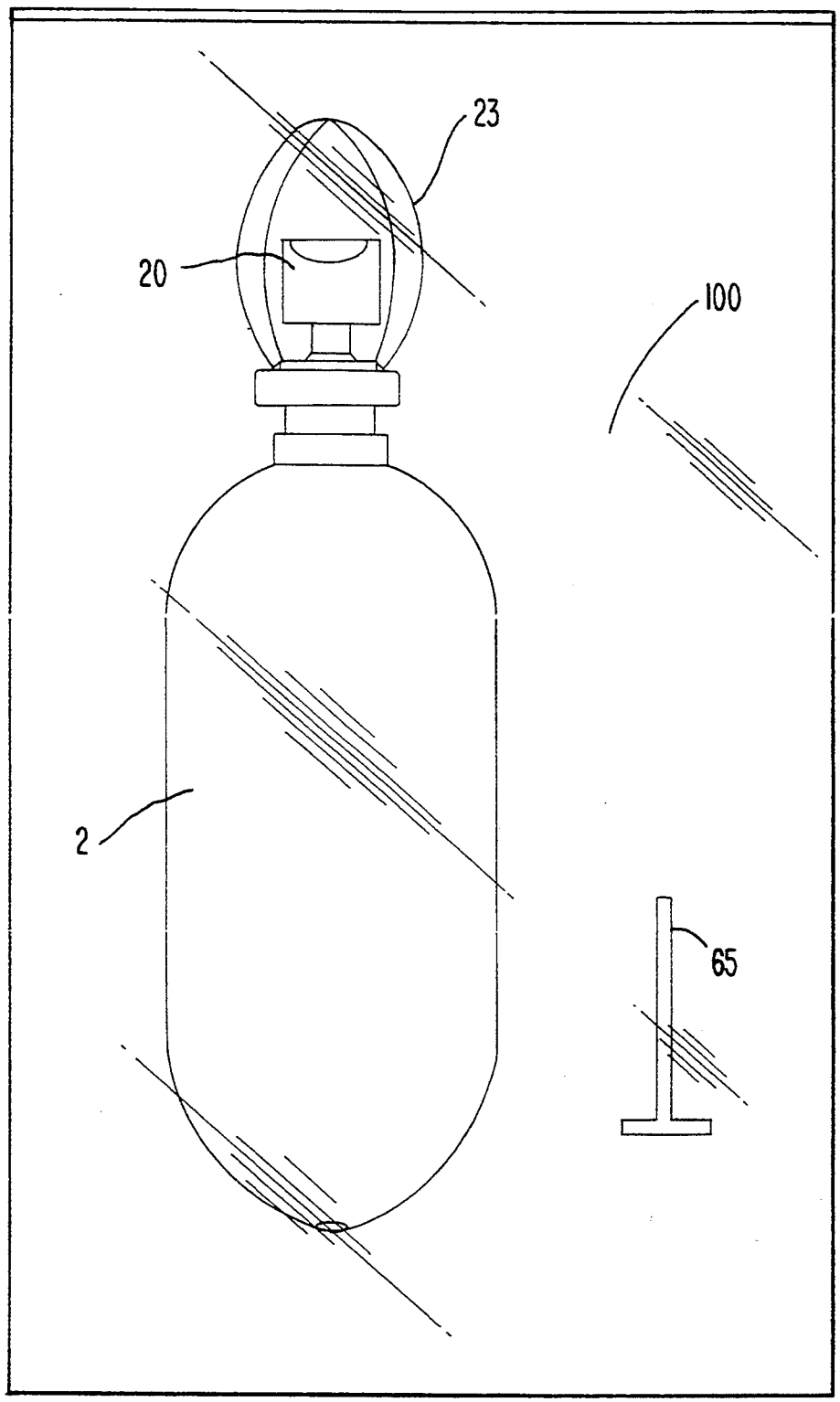
FIG. 6 is an elevational view of the dispenser of FIG. 1 packaged in a sterile pouch.

As shown in FIG. 6, in a preferred embodiment, dispenser 1 is packaged, prefilled, in a sealed peel-back pouch 100 which is sterilizable and made of Tyvek ® or some other suitable material well known in the art. Pouch 100, containing a filled container 2, nozzle 20 with shield 23 and tube 65, is sealed and then irradiated or bombarded with electron beams to sterilize the apparatus and the stored fluid. To use, the care giver merely opens the pouch 100 and removes the apparatus.

As shown in FIG. 6, shield 23 is folded back upon itself to provide a more compact package. This preferred embodiment of shield 23 requires that the shield comprise an elastically deformable material, most preferably the styrene ethylene-butylene styrene block copolymer identified earlier. Polyvinyl chloride is a less preferred material for shield 23.

To irradiate the dispensers, the packaged dispensers are loaded into a tote. The loaded totes are exposed to Cobalt 60 several times in a manner known in the art. The packages are thus exposed to gamma radiation such that the dispenser, the wound cleansing solution in the dispenser, and the pouch are all sterilized, preferably to a sterility assurance level of $10^{-6}$ (a measurement of microbial inactivation used by those skilled in the art). However, other recognized standards of sterility would also be acceptable as required by the intended use of the dispenser. Such irradiation can be performed by a contract sterilization facility such as Isomedix, Inc. of Whippany, N.J.

Once pouch 100 and dispenser 1 have been sterilized, the pouch maintains the entire dispenser (i.e., the outside surface as well as its contents) in a sterile condition until use. Consequently, the dispenser may be used in a sterile environment such as a hospital operating room. One person can open the pouch without touching the dispenser. The care giver, who would be scrubbed and gloved, can then grab the sterile dispenser without touching the non-sterile outer surface of the pouch. In this way, the outer surface of the pouch may be non-sterile but the entirety of the dispenser remains sterile.

The dispenser 1 also may be sold, empty, in a sealed pouch 100. The pouch, containing an empty container 2, nozzle 20 with spray shield 23, and extender tube 65, is sterilized in the manner described above. The dispenser may be removed from a pouch and filled through the nozzle at the point of use. This requires a supply of cleansing fluid, which could be an IV bag, a pump, a filling pin releasably engagable with nozzle 20, and necessary tubing from the supply to the pump and from the pump to the filling pin. Sealed pouch 100 may be provided with a sterile injection port covered by a tear-off patch and removably connected to nozzle 20 for aseptic filling through the pouch just prior to use by the care giver.

FIG. 7 shows dispenser 1 of the present invention mounted on stand 120 to keep spray shield 23 and nozzle 20 from contacting any non-sterile field when the dispenser is rested on a non-sterile surface, such as a hospital table. Stand 120 comprises foot 121 and arm 122. Foot 121 is disposed on the surface on which dispenser 1 is to be rested. Arm 122 is attached to foot 121 at an angle such that the arm protrudes up away from the surface. Sleeve 4 of the dispenser is laid on arm 122, the bottom end of the sleeve resting on the surface. The top end of sleeve 4, and thus nozzle 20 and spray shield 23 there located, are held aloft of the non-sterile surface. Consequently, nozzle 20 and spray shield 23 can be rested on a non-sterile surface and yet be maintained in a sterile condition.

As shown in FIG. 1, the exterior of sleeve 4 is cylindrical when not inflated. Alternately, as shown in FIG. 7, spokes 130 may be mounted on the exterior of sleeve 4, extending the length of the sleeve. The spokes prevent the container 2 from rolling along a surface when placed down. As shown in FIG. 7, there are three spokes. Of course, any number of spokes that prevent container 2 from rolling would suffice. Further, spokes 130 need not extend the entire length of sleeve 4 to prevent rolling of container 2.

Applicant's invention is not limited to the embodiments described above, but it is understood that applicant's invention is as set forth in the following claims.

I claim:

1. A portable, non-aerosol, incineratable wound cleansing liquid dispenser consisting essentially of:
    actuatable, elastomeric container means for holding and selectively delivering sterile wound cleansing liquid at a substantially constant liquid pressure;
    spokes mounted at the exterior of said container means and extending longitudinally along said container means adapted to prevent said container from rolling;
    nozzle means in fluid communication with said container means for selectively actuating said container means to discharge therefrom, through said nozzle means, wound cleansing liquid in a directed liquid stream at a substantially constant stream pressure of about 8 psig; and
    shield means mounted on said nozzle means for protecting a care giver from splashing;
    whereby said container means shrinks as wound cleansing liquid is discharged, thereby providing a visual indication of wound cleansing liquid held in said container means.

2. The dispenser of claim 1 wherein said nozzle means is further capable of discharging wound cleansing liquid in a directed liquid stream at an additional substantially constant stream pressure of less than 8 psig.

3. The dispenser of claim 1 wherein said shield means is flexible.

4. The dispenser of claim 1 wherein said container means has a capacity to hold about 200–250 ml of wound cleansing liquid.

5. A portable, non-aerosol wound cleansing solution dispenser comprising:
    an elastomeric container having a resiliently expandable outer wall, comprising:
    spokes mounted to the outer wall and extending longitudinally along said outer wall adapted to prevent said container from rolling,
    a flexible, generally cylindrical fluid container comprising a non-reactive, non-contaminating material having a pressure resistant .closed end and an open end having a neck,
    a valve assembly sealingly engaged in said neck,
    a valve, mounted within said valve assembly, actuatable from a normally closed position to an open position,
    a supply of wound cleansing solution disposed in said fluid container under pressure,
    an expanded elastomeric cylinder coaxially enclosing said generally cylindrical fluid container, said elastomeric cylinder comprising said outer wall;
    a nozzle mounted on said valve assembly, actuatingly engageable with said valve for selectively delivering wound cleansing solution from said supply; and
    a transparent spray shield mounted on said nozzle to prevent splashing onto a care giver.

6. The dispenser of claim 5, wherein said dispenser is incineratable after use.

7. The dispenser of claim 5 wherein said nozzle is further capable of discharging wound cleansing solution at a substantially constant stream pressure of about 8 psig.

8. The dispenser of claim 5 further comprising an extender tube which is attached to the nozzle for directing the solution steam.

9. The dispenser of claim 5 wherein said spray shield is a flexible spherical segment having a width of about four inches.

10. The dispenser of claim 9 further comprising a sterilizable pouch enveloping said dispenser wherein the entire dispenser is maintained in a sterile condition.

11. The dispenser of claim 5 wherein said supply of wound cleansing solution is about 200–250 ml.

12. The dispenser of claim 5 further comprising a stand adapted to support said container on a surface such that said nozzle and said spray shield are disposed away from the surface.

13. A portable device for dispensing wound cleaning liquid at a substantially constant stream pressure comprising:
    an expandable elastomeric cylinder having a first end and a second end and an axis wherein a bore is disposed at the axis which bore extends from the first end of the cylinder to the second end of the cylinder;
    spokes mounted to the exterior of the elastomeric cylinder extending longitudinally from the first end to the second end;
    a flexible generally cylindrical bag capable of containing a volume of fluid disposed within the bore, the bag having a neck positioned near one end of the cylinder and wherein the bag is composed of a non-reactive, non-contaminating material;
    a valve assembly sealingly mounted in the neck;
    a valve, mounted within the valve assembly, which valve has an open position wherein liquid can flow through the valve assembly and a closed position wherein liquid is retained in the bag;
    a nozzle actuatingly engaged to the valve, having a fluid flow path disposed therein; and
    a transparent spray shield mounted on the nozzle to prevent liquid from splashing onto a care giver,
    whereby said elastomeric cylinder shrinks as wound cleansing liquid is discharged, thereby providing a visual indication of wound cleansing liquid held in said cylindrical bag;
    a stand comprising a foot mounted to an arm adapted to support the container without locking engagement.

14. The device of claim 13, wherein said device is incineratable.

15. The device of claim 13 wherein said nozzle further comprises a control rod, disposed within the fluid flow path which is displaceable from a first position blocking a first portion of the fluid flow path to a second position blocking a second portion of the fluid flow path, wherein said first portion is larger than the said second portion.

16. Apparatus according to claim 13 further comprising a sterilizable pouch enveloping the device.

17. Apparatus according to claim 16 further comprising an extender tube disposed within said pouch, which tube is attachable to said nozzle.

18. The device of claim 13 wherein said spray shield is flexible.

19. The device of claim 13 wherein the liquid exits said fluid flow path at a substantially constant stream pressure of about 8 psig.

20. The device of claim 13 wherein said bag has a capacity to hold about 200–250 ml of wound cleansing fluid.

* * * * *